United States Patent [19]

Hackl et al.

[11] Patent Number: 5,283,362

[45] Date of Patent: Feb. 1, 1994

[54] PROCESS FOR THE PREPARATION OF PURE N,N'-ASYMMETRICALLY SUBSTITUTED PHENYLUREAS

[75] Inventors: Kurt A. Hackl; Heinz Falk, both of Linz, Austria

[73] Assignee: Chemie Linz Gesellschaft m.b.H., Linz, Austria

[21] Appl. No.: 922,767

[22] Filed: Jul. 31, 1992

[30] Foreign Application Priority Data

Aug. 16, 1991 [AT] Austria ................... 1616/91

[51] Int. Cl.$^5$ ................... C07C 273/18; C07C 275/26; C07C 275/28
[52] U.S. Cl. ......................... 564/48; 564/47; 564/50; 564/52; 564/53; 564/54; 548/200; 548/538; 546/226; 544/390; 544/165; 544/59
[58] Field of Search .................. 564/48, 50, 52, 53, 564/54; 548/538, 200; 546/226; 544/390, 59, 165

[56] References Cited

U.S. PATENT DOCUMENTS

| | | | |
|---|---|---|---|
| 3,935,258 | 1/1976 | Hempel et al. | 564/52 |
| 4,410,697 | 10/1983 | Török et al. | 564/53 |
| 4,814,499 | 3/1989 | Parron | 564/52 |
| 5,043,444 | 8/1991 | Mullner et al. | 544/169 |
| 5,091,553 | 2/1992 | Mullner et al. | 558/302 |
| 5,099,021 | 3/1992 | Worther et al. | 546/198 |

FOREIGN PATENT DOCUMENTS

| | | | |
|---|---|---|---|
| 1064051 | 8/1959 | Fed. Rep. of Germany | |
| 166326 | 11/1964 | U.S.S.R. | 564/48 |
| 178367 | 1/1966 | U.S.S.R. | |

OTHER PUBLICATIONS

Davis et al., "J. Am. Chem. Soc.", 44 2595 (1922).

Primary Examiner—Richard J. Raymond
Assistant Examiner—Shailendra Kumar
Attorney, Agent, or Firm—Wenderoth, Lind & Ponack

[57] ABSTRACT

Process for the preparation of very pure ureas of the formula phenyl—$(NH-CO-NR_1R_2)_n$ in which phenyl represents an unsubstituted or substituted phenyl or phenylene group and $R_1$ and $R_2$ are either identical and each represent an alkyl group, or are different, in which case $R_1$ represents a hydrogen atom and $R_2$ represents an alkyl or phenyl group, or $R_1$ and $R_2$, together with the nitrogen atom, represent an aliphatic heterocyclic ring and n is the number 1 or 2, by reacting a phenylurea of the formula phenyl—$(NH-CO-NH_2)_n$ with an amine of the formula $NR_1R_2H$ at temperatures from 100 to 200° C. in a diluent which is inert under the reaction conditions, the reaction being interrupted before by-products are formed, and the urea which is formed being removed from the starting compounds, and the unreacted starting compounds being returned to the process if appropriate.

10 Claims, No Drawings

PROCESS FOR THE PREPARATION OF PURE N,N'-ASYMMETRICALLY SUBSTITUTED PHENYLUREAS

The invention relates to a process for the preparation of pure N,N'-asymmetrically substituted phenylureas from phenylureas and amines.

N,N'-asymmetrically substituted phenylureas are biologically active and are used for example as herbicides. A process for the preparation of N,N'-asymmetrically substituted phenylureas from an alkylurea and an optionally substituted amine is known for example from German Patent 1 064 051. This describes that urea is reacted with an equivalent amount of a mono- or dialkylamine in aqueous solution and the alkylurea is heated with an equimolar amount of an aniline until the evolution of ammonia has ceased.

According to U.S. Pat. No. 4,814,499 N,N'-asymmetrically substituted phenylureas may be prepared by simultaneous reaction of urea with an aniline and an appropriate secondary amine in a solvent which does not contain hydroxyl groups. SU-178 367 describes the preparation of N-p-chlorophenyl-N',N'-dimethylurea by the reaction of urea in trichlorobenzene with an excess of p-chloroaniline and subsequent introduction of a large excess of dimethylamine into the reaction mixture at temperatures from 175° to 202° C. However, the products which are formed using the abovementioned processes are always contaminated with by-products which are difficult to remove. This is not surprising since, according to Davis et al., J. Am. Chem. Soc. 44, 2595, 1922, heating of urea with an amine gives isocyanuric acid, and heating of a monosubstituted urea with an amine gives the corresponding isocyanate as an intermediate, before conversion to the N,N'-asymmetrically substituted phenylurea can take place. Since isocyanuric acid and isocyanates are very reactive and react in a non-specific manner, the formation of by-products, for example biuret derivatives, must take place right from the start of the reaction. Such by-products, which contaminate the desired phenylurea, are generally very difficult, if not impossible, to separate off.

Unexpectedly, it has now been found that the reaction of phenylureas with an amine in an inert solvent at temperatures from 100° to 200° C. does not proceed via the intermediate isocyanate, which is the trigger for the formation of a very wide range of by-products, but directly by nucleophilic substitution. As long as the rate of reaction, which is associated with the concentration of the starting materials, does not slow down, i.e. as long as the concentration of starting materials is sufficiently large, no by-products at all are formed. Up until the time at which the reaction mixture becomes too depleted in starting material, the reaction mixture only contains pure starting material, pure end product and the solvent being used.

Therefore, if the reaction of phenylureas with an amine is terminated before the reaction is depleted in starting material, a mixture of pure starting materials and pure end product is obtained, with virtually no by-products. Since an N,N'-asymmetrically substituted phenylurea, due to its specific chemical constitution, can be very easily separated from the starting materials, that is to say from the phenylurea and the amine, very pure N,N'-asymmetrically substituted phenylurea is obtained in this way. The unreacted starting compounds, which are also present in very pure form, are returned to the reaction together after removal of the N,N'-asymmetrically substituted phenylurea formed, so that finally very pure N,N'-asymmetrically substituted phenylurea may be prepared virtually quantitatively. It is essential in this method that a phenylurea reacts with an amine and not an alkylurea with an aniline. In fact, the reaction of an alkylurea with an aniline in general only proceeds at more elevated temperatures than the reaction of phenylurea with an alkylamine, and by-products are formed from the start.

The invention therefore relates to a process for the preparation of pure N,N'-asymmetrically substituted phenylureas of the formula

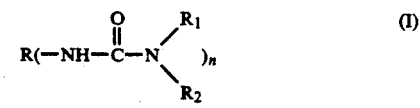

in which R represents a phenyl or phenylene group which is unsubstituted or substituted by groups which are inert under the reaction conditions and $R_1$ and $R_2$ are either identical and each represent an alkyl group or are different, $R_1$ representing a hydrogen atom or an alkyl group and $R_2$ representing an alkyl or phenyl group, or $R_1$ and $R_2$, together with the nitrogen atom, represent an aliphatic, heterocyclic ring and n is the number 1 or 2, comprising reacting a phenylurea of the formula

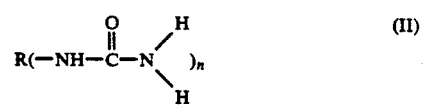

in which R and n have the abovementioned meaning, with an amine of the formula

in which $R_1$ and $R_2$ have the abovementioned meaning, at temperatures from 100° to 200° C. in a diluent which is inert under the reaction conditions, interrupting the reaction before by-products are formed, removing the N,N'-asymmetrically substituted phenylurea of the formula I from the reaction mixture, and, if appropriate, returning the unreacted starting compounds of the formulae II and III to the process.

In formula I, R represents a phenyl or phenylene group which is unsubstituted or substituted by groups which are inert under the reaction conditions. Groups which are inert under the reaction conditions are for example halogen atoms, alkyl groups, aryl groups, alkoxy groups, aryloxy groups, amino groups which are substituted by groups which are inert under the reaction conditions, such as alkyl-, aryl -, nitro groups. The alkyl, aryl, alkoxy or aryloxy groups may in turn be substituted by inert groups such as those mentioned above. Halogen atoms are taken to mean in particular fluorine, chlorine or bromine, and alkyl or alkoxy groups are taken to mean straight-chain, branched or cyclic alkyl or alkoxy groups.

R preferably represents a phenyl or phenylene group which is unsubstituted or substituted by halogen atoms, alkyl groups with 1 to 6 C atoms, the trifluoromethyl group, alkoxy or 1 dialkylamino groups, the alkyl groups possessing 1 to 6 C atoms, more preferably 1 to 3 C atoms.

$R_1$ and $R_2$ are either identical and each represents an alkyl group which is unsubstituted or is substituted by groups which are inert under the reaction conditions, such as those mentioned above, or $R_1$ and $R_2$ are different and $R_1$ represents a hydrogen atom or an alkyl group and $R_2$ represents an alkyl or phenyl group, it being possible for the alkyl groups and/or phenyl groups to be unsubstituted or substituted by groups which are inert under the reaction conditions, such as those mentioned above, or $R_1$ and $R_2$, together with the nitrogen atom, represent an aliphatic heterocyclic ring, which may include further hetero atoms and which may be unsubstituted or substituted by groups which are inert under the reaction conditions, such as those mentioned above. Examples of aliphatic heterocyclic rings are for instance pyrrolidine, piperidine, piperazine, morpholine, thiazolidine, and thiomorpholine rings. In formulae I and II, n is the number 1 or 2. Alkyl groups in this instance are taken to mean straight-chain, branched or cyclic alkyl groups, preferably straight-chain or branched alkyl groups. If $R_1$ and $R_2$ are identical, $R_1$ and $R_2$ preferably represent unsubstituted, straight-chain alkyl groups with 1 to 18, more preferably with 1 to 12 C atoms. If $R_1$ and $R_2$ are different, $R_1$ preferably represents a hydrogen atom and $R_2$ represents a straight-chain alkyl group with 1 to 22 C atoms, a branched alkyl group with 1 to 8, more preferably with 1 to 6 C atoms or a phenyl group which is unsubstituted or substituted by halogen atoms, alkyl groups with 1 to 6 C atoms, alkoxy or dialkylamino groups, the alkyl groups possessing 1 to 6 C atoms. If $R_1$ and $R_2$, together with the nitrogen atom, represent an aliphatic heterocyclic ring, more preferably a pyrrolidine, piperidine or morpholine ring.

To prepare N,N'-asymmetrically substituted phenylureas of the formula I, a phenylurea of the formula II is allowed to react with an amine of the formula III at temperatures from 100° to 200° C. in a diluent which is inert under the reaction conditions.

Phenylureas of the formula II may be prepared for example from appropriately substituted anilines by reaction with isocyanuric acid, for example by the procedure disclosed in U.S. Pat. No. 5,043,444. Amines of the formula III are known or may be obtained using known methods.

The phenylurea of the formula II is introduced into a diluent which is inert under the reaction conditions and treated with an amine of the formula III. The amine may be added as such, in the solid, liquid or gaseous state, or dissolved in an inert diluent. The amine of the formula III is preferably employed in an equivalent amount to the phenylurea of the formula II, but an excess of one or other of the reactants may be advantageous. If a urea of the formula II in which n is the number 2 is used, it is likewise preferred to employ equivalent amounts, i.e., one mole of amine of the formula III is used per mole of free amino group. Suitable diluents are diluents which are inert under the reaction conditions and which have a boiling point above 100° C. Examples of such diluents are hydrocarbons, halogenated hydrocarbons, preferably aromatic hydrocarbons and more preferably toluene or xylenes.

The reaction mixture is advantageously heated with vigorous stirring, if appropriate under pressure, at temperatures from 100° to 200° C., preferably from 110° to 160° C., particularly preferably at the reflux temperature of the inert diluent being used. If the reaction is performed under pressure, it is preferably performed in an autoclave under autogenous pressure.

In this way, the urea of the formula I and one mole of ammonia per mole of urea, are formed without any by-products being obtained for the time being. From the beginning of the reaction onwards, the reaction mixture contains only pure end product, along with pure starting compounds, the solvent being used and possibly ammonia. Only from the time at which the reaction becomes too depleted in starting materials are by-products formed. This time depends on the type of solvent, the reaction temperature and on the initial concentration, molar ratio and chemical nature of the particular starting compounds and may easily be determined for any desired reaction according to the invention by means of a preliminary test which is monitored analytically, for example chromatographically, especially by gas chromatography. The reaction according to the invention is then performed as in the preliminary test and is interrupted shortly before reaching the time from which by-products are obtained, as determined in the preliminary test.

Virtually no by-products are obtained during the course of the process owing to the arbitrary termination of the reaction in good time.

The ammonia produced during the course of reaction is either removed continuously as a gas or, if the reaction was performed under pressure, is removed after the end of the reaction. The ammonia may be collected and used in a customary application.

To study the reaction mechanism, 4-methoxyphenylurea was heated in boiling toluene. It was expected that 4-methoxyphenyl isocyanate would be formed, but instead the 4-methoxyphenylurea remained completely unchanged. On heating 4-methoxyphenylurea in boiling toluene with the addition of one equivalent of dioctylamine, N,N-dioctyl-N'-4-methoxyphenylurea was formed in 60% yield after one hour, no by-products, in particular no isocyanates or by-products derived from them, being produced. Proof that the reaction does not proceed via isocyanates was obtained using $^1$H-NMR and $^{13}$C-NMR spectroscopy.

To determine the order of reaction, kinetic studies were performed during the reaction of phenylurea and dioctylamine in boiling toluene. Samples were withdrawn from the reaction mixture after specific intervals of time, the solvent was evaporated off and the residue taken up and digested in $CDCl_3$. Since phenylurea is virtually insoluble in deuterated chloroform, but dioctylamine and N-phenyl-N',N'-dioctylurea are very soluble, the particular molar ratio of dioctylamine and N-phenyl-N',N'-dioctylurea, and thus the extent of conversion, may be determined directly in the $CDCl_3$ extract, using $^1$H-NMR spectroscopy, by integration of the signals from the N—$CH_2$ protons (dioctylamine 2.57 ppm, N-phenyl-N',N'-dioctylurea 3.28 ppm).

On evaluating the kinetic study according to A.A. Frost and R.G. Pearson, "Kinetics and mechanism of homogeneous reactions", Verlag Chemie, Weinheim, 1984, it was found that the rate of reaction depends both on the concentration of dioctylamine and also on that of phenylurea and that the measured results can be correlated well with a second order reaction mechanism. All other observations also pointed to a direct nucleophilic substitution (bimolecular reaction), it being found that the following relationship holds:

$$\frac{d(\text{N'-phenyl-N,N-dioctylurea})}{dt} = k_2 \cdot (\text{phenylurea}) \cdot (\text{dioctylamine})$$

with $k_2$ in this case being approximately 0.3 1 mol$^{-1}$.sec$^{-1}$. The formula holds good for concentrations of approximately 0.1 to 0.2 mol per liter. The reaction therefore proceeds as a 2nd order reaction.

The reaction is interrupted stopping the heating and if necessary by cooling the reaction mixture. After interrupting the reaction the N,N'-asymmetrically substituted urea is separated from the unconverted starting compounds of the formulae II and III, if necessary after expelling any ammonia which is still present.

In many cases this may be accomplished merely by cooling the reaction mixture, since the phenylurea of the formula II frequently precipitates out on cooling while the N,N'-asymmetrically substituted urea and the amine of the formula III remain in solution. After filtering off the urea of the formula II, the amine of the formula III may then be removed by extraction or by distillation, and the N,N'-asymmetrically substituted urea of the formula I is obtained in pure form.

However, the reaction mixture may also be separated extractively. N-Phenyl-N'-alkyl- and N-phenyl-N'-dialkylureas are for example soluble in chloroform if the alkyl groups have a chain with 3 or more C atoms, whereas N-phenylureas are sparingly soluble. N-phenyl-N'-phenylurea may generally be separated from phenylurea by extraction with water. Furthermore, the reaction mixture may also be separated using chromatographic methods, for example by column chromatography or if desired by crystallographic methods, for instance fractional crystallization.

The reaction may be performed batchwise or continuously.

Since no by-products are formed in the course of the reaction according to the invention, the N,N'-asymmetrically substituted urea is obtained in very pure form. The starting compounds of the formulae II and III, which remain in the reaction mixture in very pure form, are reintroduced into the reaction according to the invention after the product has been removed from the reaction mixture.

N,N'-asymmetrically substituted phenylureas can be prepared without by-products, and therefore in very pure form and virtually quantitatively, in the type of reaction procedure which is described. The process therefore represents an enrichment of the art.

EXAMPLE 1

1.36 g of phenylurea (10 mmol) and 2.41 g of dioctylamine (10 mmol) were heated under reflux in 50 ml of xylene, with vigorous stirring. After 30 minutes a conversion of 70% and after 60 minutes a conversion of 83% was achieved, without by-products having been formed. The ammonia formed during the reaction was removed in gaseous form.

After 60 minutes the reaction was interrupted and the solvent evaporated off. The residue was taken up in chloroform and the insoluble phenylurea was filtered off. The chloroform was evaporated from the filtrate and the unconverted dioctylamine was removed by distillation under high vacuum.

3.00 g of N-phenyl-N',N'-dioctylurea which is 83% of the maximum theoretical yield, and of virtually 100% purity were obtained in this way.

$^1$H-MR (200 MHz; CDCl$_3$; TMS): 7.378 (m; 2H; phenyl-2 and 6; $J_{2,3\text{-}ortho}=8.4$ Hz; $J_{meta}=1.3$ Hz; 7.264 (m; 2H; phenyl-3 and 5; $J_{2,3\text{-}ortho}=8.4$ Hz; $J_{3,4\text{-}ortho}=7.2$ Hz); 7.002 (m; 1H, phenyl-4; $J_{meta}=1.3$ Hz; $J_{3,4\text{-}ortho}=7.2$ Hz); 6.294 (s; 1H; NH); 3.274 (t; 4H; octyl-1; $J_{CH_2CH_2}=7.4$ Hz); 1.605 (tt; 4H; octyl-2; $J_{CH_2CH_2}=7.4$ Hz); 1.294 (m; 20H; octyl-3–7; $J_{CH_2CH_2}=6.3$ Hz); 0.882 (t; 6H, octyl-8; $J_{CH_2CH_3}=6.3$ Hz) ppm.

Furthermore, 0.23 g of phenylurea, which is 17 mol-% of the amount used, and 0.41 g of dioctylamine, which is 17 mol-% of the amount used, were recovered.

EXAMPLE 1a–1d

Phenylurea and dioctylamine were heated in xylene, with vigorous stirring, under various conditions. Samples were withdrawn from the mixture after specific reaction times, the solvent was evaporated from each of the samples at 65° C. in vacuo and the residue was taken up in CDCl$_3$, in which phenylurea is virtually insoluble and in which N-phenyl-N',N'-dioctylurea and dioctylamine on the other hand are completely soluble. The precipitated phenylurea was filtered off and a $^1$H-NMR spectrum of the filtrate was prepared. The particular molar ratio of dioctylamine to the N-phenyl-N',N'-dioctylurea formed was determined by integrating the signals from the —N—CH$_2$ protons of the dioctylamine (2.75 ppm) and the N-phenyl-N',N'-dioctylurea formed (3.28 ppm), from which was derived the degree of conversion.

In Example 1a the conversion (C) at different initial concentrations of the reactants phenylurea (A) and dioctylamine (B) was measured in the solvent, the measurements being taken after 15 minutes in each case. The values given in Table 1a were obtained in this way:

TABLE 1a

| A (mol/l) | B (mol/l) | C after 15 minutes (%) |
|---|---|---|
| 0.1 | 0.1 | 41.5 |
| 0.2 | 0.2 | 44.6 |
| 1.0 | 1.0 | 56.0 |

In Example 1b, C was measured at different initial molar ratios of the reactants A and B, the measurements being made after 15 minutes in each case. The results are given in Table 1b:

TABLE 1b

| A (mol/l) | B (mol/l) | A:B | C after 15 minutes (%) |
|---|---|---|---|
| 0.1 | 0.1 | 1:1 | 41.5 |
| 0.1 | 0.2 | 1:2 | 40.4 |
| 0.1 | 0.5 | 1:5 | 56.0 |
| 0.1 | 1.0 | 1:10 | 73.3 |
| 0.2 | 0.2 | 1:1 | 44.6 |
| 0.2 | 0.4 | 1:2 | 55.3 |
| 0.7 | 0.5 | 14:10 | 44.2 |
| 0.7 | 1.0 | 7:10 | 59.6 |

In Example 1c, C was measured after different reaction times (t), with identical initial concentrations of the reactants A and B giving the values shown in Table 1c.

TABLE 1c

| A (mol/l) | B (mol/l) | t (minutes) | C (%) |
|---|---|---|---|
| 0.1 | 0.1 | 5 | 12.9 |
| 0.1 | 0.1 | 10 | 28.1 |

TABLE 1c-continued

| A (mol/l) | B (mol/l) | t (minutes) | C (%) |
| --- | --- | --- | --- |
| 0.1 | 0.1 | 15 | 41.5 |
| 0.1 | 0.1 | 20 | 49.1 |
| 0.1 | 0.1 | 25 | 58.9 |
| 0.1 | 0.1 | 30 | 68.6 |
| 0.1 | 0.1 | 40 | 75.6 |
| 0.1 | 0.1 | 60 | 83.3 |

In Example 1d, C was measured at two different reaction temperatures (T) after different reaction times (t), the initial concentration of the reactants in the solvent being 0.2 mol/l in each case, giving values shown in Table 1d:

TABLE 1d

| t (minutes) | T (°C.) | Conversion (%) |
| --- | --- | --- |
| 3 | 120 | 1.6 |
|  | 130 | 11.7 |
| 13 | 120 | 8.9 |
|  | 130 | 29.4 |
| 23 | 120 | 16.6 |
|  | 130 | 42.1 |
| 33 | 120 | 22.7 |
|  | 130 | 47.2 |
| 43 | 120 | 29.3 |
|  | 130 | 53.9 |

EXAMPLE 2

Performed as described in Example 1, but using 4-methoxyphenylurea instead of phenylurea, N-(4-methoxyphenyl)-N',N'-dioctylurea being obtained. The conversion after 30 minutes was about 60%.

$^1$H-NMR (200 MHz; DMSO; TMS): 7.944 (s; 1H; NH); 7.305 and 6.780 (m; each 2H; methoxyphenyl-2,3,5 and 6; $J_{ortho}$=0.9 Hz); 3.681 (s; 3H; methoxy-CH$_3$); 3.223 (t; 4H; octyl-1; $J_{CH2CH2}$=7.2 Hz); 1.462 (m; 4H; octyl-2; $J_{CH2CH2}$=7.2 Hz); 1.236 (m; 20H, octyl-3–7; $J_{CH2CH3}$=6.4 Hz); 0.838 (t; 6H; octyl-8; $J_{CH2CH3}$=6.4 Hz) ppm.

EXAMPLE 3

Performed like Example 1, but using diethylamine instead of dioctylamine and chlorophenylurea instead of phenylurea, N-(4-chlorophenyl)-N',N'-diethylurea being obtained.

$^1$H-NMR (200 MHz; CDCl$_3$; TMS): 7.336 and 7.198 (m; each 2H; phenyl-2,3,5 and 6; $J_{ortho}$=9.0 Hz); 6.473 (s; 1H; NH); 3,344 (q; 4H; ethyl-1; Hz); 1.191 (t; 6H; ethyl-2; $J_{CH2CH3}$=7.0 Hz) ppm.

EXAMPLE 4

Performed like Example 1, but using 4-chlorophenylurea instead of phenylurea, N-(4-chlorophenyl)-N',N'-dioctylurea being obtained. The conversion after 30 minutes was about 20%.

$^1$-H-NMR (200 MHz; DMSO; TMS): 8.231 (s; 1H; NH); 7.477 and 7.235 (m; each 2H; chlorophenyl-2,3,5 and 6; $J_{ortho}$=8.9 Hz); 3.244 (t; 4H; octyl-1; $J_{CH2CH2}$=7.2 Hz); 1.459 (m; 4H; octyl-2; $J_{CH2CH2}$=7.2 Hz); 1.226 (m; 20H; octyl-3–7; $J_{CH2CH3}$=6.4 Hz); 0.830 (t; 6H, octyl-8; $J_{CH2CH3}$=6.4 Hz) ppm.

EXAMPLE 5

1.36 g of phenylurea (10 mmol) and 0.73 g of tert.butylamine (10 mmol) were heated under reflux in 50 ml of xylene, with vigorous stirring. The ammonia formed in this way was removed as a gas. After 30 minutes a conversion of about 50% was achieved, without by-products being produced, and the reaction was interrupted, the solvent and unconverted tert.butylamine evaporated off under vacuum and the residue taken up in chloroform. Thus the N-phenyl-N,-tert.butylurea dissolved while the unconverted phenylurea precipitated out and was filtered off. The chloroform solution was evaporated down and the residue was recrystallized from ethanol in order to remove any tert.butylurea which had not evaporated.

0.90 of N-phenyl-N'-tert.butylurea, which is 47% of maximum theoretical yield with a purity of virtually 100% was obtained.

$^1$H-NMR (200 MHz; DMSO; TMS): 8.205 (s; 1H; phenyl-NH); 7.343 (m; 2H; phenyl-2 and 6; $J_{2,3\text{-}ortho}$=8.0 Hz); $J_{meta}$=1,1 Hz); 7.185 (m; 2H; phenyl-3 and 5; $J_{2,3\text{-}ortho}$=8.0 Hz; $J_{3,4\text{-}ortho}$=7.3 Hz); 6.847 (m; 1H; phenyl-4; $J_{meta}$=1,1 Hz; $J_{3,4\text{-}ortho}$=7.3 Hz); 5.965 (s; 1H; tert.butyl-NH); 1.280 (s; 9H; tert.butyl-CH$_3$) ppm.

Furthermore, 0.38 g of tert.butylamine, which is 52 mol-% of the amount used initially, and 0.72 g of phenylurea, which is 53 mol-% of the amount used initially, were recovered.

EXAMPLE 6

Performed like Example 1 but using octadecylamine instead of dioctylamine, N-phenyl-N'-octadecylurea being obtained.

$^1$H-NMR (200 MHz; pyridine-d5; TMS): 9.259 (s; 1H; phenyl-NH); 7.913 (m; 2H; phenyl-2 and 6; $J_{2,3\text{-}ortho}$=7.5 Hz; $J_{meta}$=1.1 Hz); 7.328 (m; 2H; phenyl-3 and 5; $J_{2,3\text{-}ortho}$=7.5 Hz; $J_{3,4\text{-}ortho}$=7.3 Hz); 7.000 (m; 1H; phenyl-4; $J_{meta}$=1.1 Hz; $J_{3,4\text{-}ortho}$=7.3 Hz); 6.564 (t; 1H; octadecyl-NH; $J_{CH2NH}$=6.0 Hz); 3.466 (dt; 2H, octadecyl-1; $J_{CH2NH}$=6.0 Hz; $J_{CH2CH2}$=6.9 Hz); 1.557 (tt; 2H; octadecyl-2; $J_{CH2CH2}$=6.9 Hz); 1.274 (m; 30H; octadecyl-3–17; $J_{CH2CH3}$=6.1 Hz); 0.873 (t; 3H; octadecyl-18; $J_{CH2CH3}$=6.1 Hz) ppm.

EXAMPLE 7

Performed as in Example 5, but using 4-methoxyphenylurea instead of phenylurea and introducing ethylamine instead of tert.butylamine, N-(4-methoxyphenyl)-N'-ethylurea being obtained.

$^1$H-NMR (200 MHz; CDCl$_3$; TMS): 7.646 (s; 1H; phenyl-NH); 7.108 and 6.732 (m; each 2H; phenyl-2,3,5 and 6; Jortho=8.9 Hz); 5.807 (t; 1H; ethyl-NH; $J_{CH2NH}$=5.1 Hz); 3.710 (s; 3H; methoxy-CH3); 3.150 (dq; 2H; ethyl-1; $J_{CH2NH}$=5.1 Hz; $J_{CH2CH3}$=7.2 Hz) 1.029 (t; 3H; ethyl-2; $J_{CH2CH3}$=7.2 Hz) ppm

EXAMPLE 8

Performed as in Example 5, but using (4-N,N-dimethylamino)-phenylurea instead of phenylurea and propylamine instead of tert.butylamine, N-(4-(N,N-dimethylamino)-phenyl)-N,-propylurea being obtained.

$^1$H-NMR (200 MHz; CDCl$_3$; TMS): 7.251 (s; 1H; phenyl-NH); 7.105 (m; 2H, phenyl-2 and 6; $J_{ortho}$=8.9 Hz); 6.627 (m; 2H; phenyl-3 and 5; $J_{ortho}$=8.9 Hz); 5.566 (t; 1H; propyl-NH; $J_{CH2NH}$5.6 Hz); 3.082 (dt; 2H; propyl-1; $J_{CH2NH}$=5.6 Hz; $J_{CH2CH2}$=7.2 Hz); 2.864 (s; 6H; dimethylamino-CH3); 1.420 (tq; 2H; propyl-2; $J_{CH2CH2}$=$J_{CH2CH3}$=7.2 Hz); 0.836 (t; 3H; propyl-3; $J_{CH2CH3}$=7.2 Hz) ppm

EXAMPLE 9

Performed as in Example 8, but using isopropylamine instead of propylamine, N-(4-(N,N-dimethylamino)- phenyl)-N'-isopropylurea being obtained. ¹H-NMR (200 MHz; DMSO; TMS: 7.890 (s; 1H; phenyl-NH); 7.170 (m; 2H; phenyl-2 and 6; $J_{ortho}=9.0$ Hz); 6.632 (m; 2H, phenyl-3 and 5; $J_{ortho}=9.0$ Hz); 5.780 (d; 1H; isopropyl-NH; $J_{CHNH}=7.6$ Hz); 3.728 (dse; 1H; isopropyl-CH; $J_{CHNH}=7.6$ Hz; $J_{CHCH3}=6.5$ Hz); 2.780 (s, 6H, dimethylamino-CH₃); 1.065 (d; 6H; isopropyl-CH₃; $J_{CHCH3}=6.5$ Hz) ppm.

EXAMPLE 10

1.36 g of phenylurea (10 mmol) and 2.41 g of 2,6-diisopropylaniline (14 mMol) were dissolved in 50 ml of xylene and heated under reflux. The ammonia formed was removed as a gas. After 30 minutes a conversion of 13% was achieved, without by-products being formed.

The reaction mixture was cooled to room temperature, the unconverted phenylurea precipitating out. After filtering, the solvent was evaporated off and the residue recrystallized from chloroform.

0.38 g of N-phenyl-N'-((2,6-diisopropyl)phenyl)-urea, which corresponds to 13% of maximum theoretical yield was obtained with virtually 100% purity.

¹H-NMR (200 MHz; DMSO; TMS): 8.757 (s; 1H; phenyl-NH); 8.318 (s; 1H; DIPP-NH); 7.467 (m; 2H; phenyl-2 and 6; $J_{2,3\text{-}ortho\,phenyl}=7.6$ Hz; $J_{meta\,phenyl}=1.0$ Hz); 7.243 (m; 2H; phenyl-3 and 5; $J_{3,4\text{-}ortho\,phenyl}=7.3$ Hz; $J_{2,3\text{-}ortho\,phenyl}=7,6$ Hz); 6.914 (m; 1H; phenyl-4; $J_{3,4\text{-}ortho\,phenyl}=7.3$ Hz; $J_{meta\,phenyl}=1.0$ Hz); 7.280 (m; 1H; DIPP-4; $J_{3,4\text{-}ortho\,DIPP}=6.8$ Hz); 7.166 (m; 2H; DIPP-3 and 5; $J_{3,4\text{-}ortho\,DIPP}=6.8$ Hz); 3.209 (se; 2H; isopropyl-CH; $J_{CHCH3}=6.9$ Hz); 1.165 (d; 12H; isopropyl-CH₃; $J_{CHCH3}=6.9$ Hz) ppm.

Furthermore, 1.15 g of unconverted phenylurea, which is 85% of the amount used initially, and 2.00 g of 2,6-diisopropylaniline, which is 83% of the amount used initially, were recovered.

EXAMPLE 11

Performed as in Example 10, but using 4-methoxyphenylurea instead of phenylurea and N,N-dimethyl-1,4-phenylenediamine instead of 2,6-diisopropylaniline, N-(4-methoxyphenyl)-N'-(4-(N,N-dimethylamino)-phenyl)urea being obtained.

¹H-NMR (200 MHz; DMSO, TMS): 8.323 and 8.205 (2s; each 1H, NH); 7.262 (m; 2H; DMAP-2 and 6; $J_{ortho\,DMPA}=9.0$ Hz); 7,352 and 6.852 (2m; each 2H; methoxyphenyl-H; $J_{ortho\,MP}=9.0$ Hz); 6.688 (m; 2H; DMAP-3 and 5; $J_{ortho\,DMPA}=9.0$ Hz); 3.706 (s; 3H, methoxy-CH₃); 2.819 (s; 6H; dimethylamino-CH₃) ppm

EXAMPLE 12

Performed as in Example 10, but using (N,N-dimethyl-amino)phenylurea instead of phenylurea and 4-chlorophenylamine instead of 2,6-diisopropylamine, N (4-(N,N-dimethylamino)-phenyl)-N'-(4-chlorophenyl-)urea being obtained.

¹H-NMR (200 MHz; DMSO; TMS): 8.667 (s; 1H; chlorophenyl-NH); 8.323 (s; 1H; DMAP-NH); 7.479 and 7.255 (2m; each 2H; chlorophenyl-2,3,5 and 6; $J_{ortho\,CP}=8.9$ Hz); 7.297 (m; 2H; DMAP-2 and 6; $J_{ortho\,DMAP}=9.0$ Hz); 6.679 (m; 2H; DMAP-3 and 5; $J_{ortho\,DMAP}=9.0$ Hz); 2.809 (s; 6H; dimethylamino-CH₃) ppm.

EXAMPLE 13

1.36 g of phenylurea (10 mmol) and 0.71 g of pyrrolidine (10 mmol) were dissolved in 50 ml of xylene and heated under reflux with vigorous stirring. The ammonia formed in this way was removed as a gas. After 30 minutes no by-products were produced (¹H-NMR and ¹³C-NMR checks) and a conversion of 40% was achieved.

The solvent and the amine were then evaporated off under vacuum and the residue was stirred thoroughly with chloroform. The N-pyrrolidinecarboxanilide formed dissolved while the phenylurea precipitated out. After filtering, the solvent was evaporated off under vacuum.

1.1 g of N-pyrrolidinecarboxanilide, which is 58% of maximum theoretical yield with a purity of virtually 100%, were obtained.

¹H-NMR (200 MHz; CDCl₃; TMS): 7.414 (m; 2H; phenyl-2 and 6; $J_{ortho}=8.1$ Hz; $J_{metal}=1.2$ Hz); 7.223 (m; 2H; phenyl-3 and 5; $J_{2,3\text{-}ortho}=8.1$ Hz; $J_{3,4\text{-}ortho}=7.5$ Hz); 6.969 (m; 1H; phenyl-4; $J_{meta}=1.2$ Hz; $J_{3,4\text{-}ortho}=7.5$ Hz); 6.543 (s; 1H; NH) 3.380 (t; 4H; pyrrolidine-2 and 5; $J_{pyr23}=6.7$ Hz); 1.860 (tt; 4H; pyrrolidine-3 and 4; $J_{pyr23}=6.7$ Hz) ppm.

Furthermore, 0.30 g of unconverted pyrrolidine, which is 42 mol-% of the amount used initially, and 0.57 g of unconverted phenylurea, which is 42 mol-% of the amount used initially, were recovered.

EXAMPLE 14

Performed as in Example 13, but using morpholine instead of pyrrolidine, N-morpholinocarbox-4-anilide being obtained. The conversion after 30 minutes was about 85%.

¹H-NMR (200 MHz; CDCl₃; TMS: 7.342−7.194 (m; 4H; phenyl-2,3,5 and 6; $J_{3,4\text{-}ortho}=8.2$ Hz; $J_{2,3\text{-}ortho}=7,3$ Hz); 7.072 (s, 1H, NH), 7.062−6.984 (m; 1H; phenyl-4; $J_{3,4\text{-}ortho}=8.2$ Hz); 3.585 (t; 2H, morpholine-CH₂—O; $J_{CH2CH2}=4.7$ Hz); 3.366 (t; 2H, morpholine-CH₂—N; $J_{CH2CH2}=4.7$ Hz) ppm.

EXAMPLE 15

2 mol of ethylamine per mole of 2,4-toluenediurea were added to a solution of 2,4-toluenediurea in xylene and the solution was heated under reflux, with vigorous stirring. The ammonia formed during the course of the reaction was removed as a gas. After 30 minutes no by-products had been produced (¹H-NMR and ¹³C-NMR checks). The solvent and the amine were then distilled off under vacuum.

2,4-bis-(diethylaminocarbamoyl)toluene was obtained.

¹H-NMR (300 MHz; CDCl₃; TMS): 7.605 (d;1H; phenyl-3; $J_{meta}=2.2$ Hz); 7.389 (dd; 1H; phenyl-5; $J_{meta}=2.2$ Hz; $J_{ortho}=8.2$ Hz); 7.032 (d; 1H; phenyl-6; $J_{ortho}=8.2$ Hz; 6.371 and 6.187 (2s; each 1H; NH); 3.409−3.292 (2q; each 4H; ethyl-1; $J_{CH2CH3}=7.2$ Hz); 2.175 (s;3H; toluene-CH₃); 1.254−1.157 (2t; each 6H; ethyl-2; $J_{CH2CH3}=7.2$ Hz) ppm.

Furthermore, toluene-2,4-diurea, N,N-diethyl-toluylene-2,4-diurea and ethylamine, but no by-products at all, were identified in the reaction mixture.

EXAMPLE 16

Performed like Example 15, but in an autoclave under autogenous pressure at 140° C. The following were detected in the reaction mixture, as well as the ammonia which was formed: 2,4-bis-(diethylaminocarbamoyl)-toluene, N,N-diethyltoluylene-2,4-diurea, 2,4-toluenediurea and ethylamine, but no by-products at all.

What is claimed is:

1. Process for the preparation of pure N,N'-asymmetrically substituted phenylureas of the formula

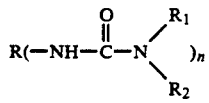

(I)

in which R represents a phenyl or phenylene group which is unsubstituted or substituted by groups which are inert under the reaction conditions and $R_1$ and $R_2$ are either identical and each represent an alkyl group or are different, $R_1$ representing a hydrogen atom or an alkyl group which can be unsubstituted or substituted by groups which are inert under the reaction conditions and $R_2$ representing an alkyl or phenyl group, either of which can be unsubstituted or substituted by groups which are inert under the reaction conditions, or $R_1$ and $R_2$, together with the nitrogen atom, represent an aliphatic heterocyclic ring and n is the number 1 or 2, said process comprising reacting a phenylurea of the formula

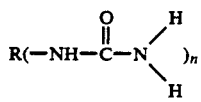

(II)

in which R and n have the abovementioned meaning, is reacted with an amine of the formula

(III)

in which $R_1$ and $R_2$ have the abovementioned meaning, at temperatures from 100° to 200° C. in a diluent which is inert under the reaction conditions, interrupting the reaction before by-products are formed, removing the N,N'-asymmetrically substituted phenylurea of the formula I from the reaction mixture and, if appropriate, returning the unreacted starting compounds of the formulae II and III to the process.

2. Process according to claim 1, comprising employing a urea of the formula II in which R represents a phenyl group which is unsubstituted or substituted by halogen atoms, alkyl groups with 1 to 6 C atoms or amino groups, each substituted by two alkyl groups possessing 1 to 3 C atoms.

3. Process according to claim 1 comprising employing an amine of the formula III in which $R_1$ and $R_2$ are identical and each represent an alkyl group with 1 to 18 C atoms.

4. Process according to claim 1 comprising employing an amine of the formula III in which $R_1$ represents a hydrogen atom and $R_2$ represents an alkyl group with 1 to 22 C atoms or a phenyl group which is unsubstituted or substituted by halogen or amino groups, each substituted by two alkyl groups possessing 1 to 3 C atoms.

5. Process according to claim 1 comprising employing an amine of the general formula III in which $R_1$ and $R_2$, together with the nitrogen atom, represent an aliphatic heterocyclic ring with 5 or 6 C atoms which may be interrupted by oxygen, sulfur or nitrogen.

6. Process according to claim 1 comprising employing the urea of the formula II and the amine of the formula III in equivalent amounts.

7. Process according to claim 1 comprising carrying out the reaction at the reflux temperature of the inert diluent used.

8. Process according to claim 1 comprising removing the ammonia formed during the reaction as a gas.

9. Process according to claim 1 comprising employing an aromatic hydrocarbon as inert diluent.

10. Process according to claim 1 comprising determining the time from which by-products are produced in a preliminary test.

* * * * *